Figure 1:
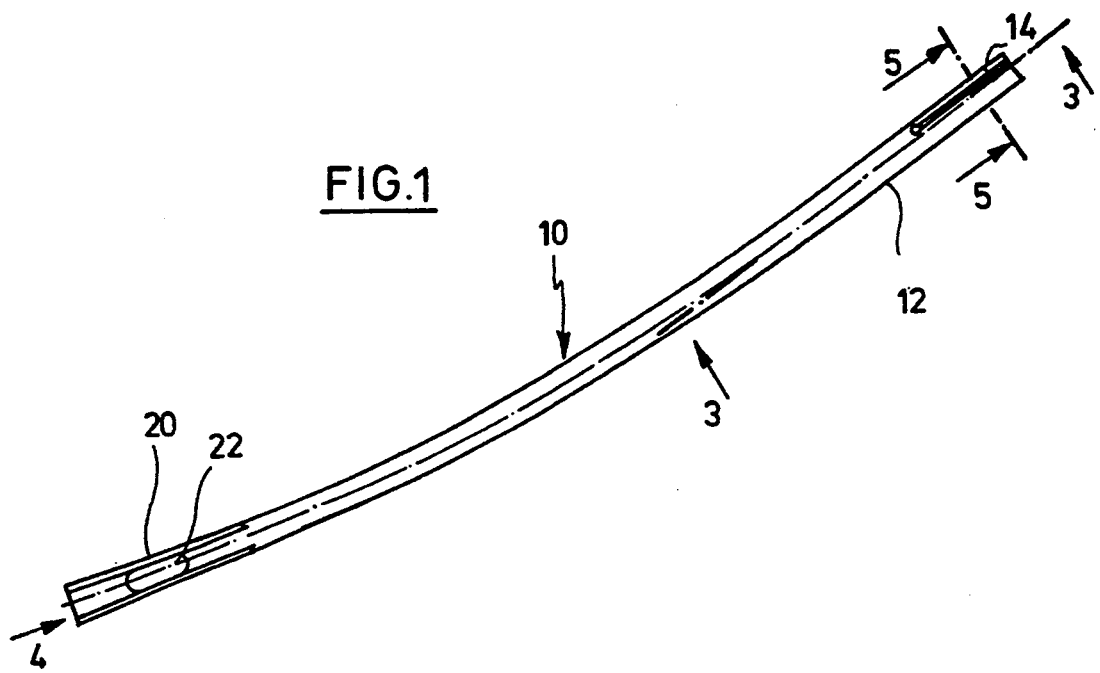

United States Patent [19]
Behrens et al.

[11] Patent Number: 5,397,328
[45] Date of Patent: Mar. 14, 1995

[54] BONE NAIL FOR SPOKE BONE FRACTURES

[75] Inventors: Klaus F. A. Behrens, Rickling, Germany; Christian Lefevre, Brest, France

[73] Assignee: Howmedica GmbH, Schoenkirche, Germany

[21] Appl. No.: 985,789

[22] Filed: Dec. 4, 1992

[30] Foreign Application Priority Data

Dec. 7, 1991 [DE] Germany .................. 9115201 U

[51] Int. Cl.⁶ .................................................. A61B 17/00
[52] U.S. Cl. .................................... 606/63; 606/60; 606/73
[58] Field of Search ............... 606/53, 60, 62, 63, 606/64, 65–68, 72, 73, 86

[56] References Cited

U.S. PATENT DOCUMENTS

| | | | |
|---|---|---|---|
| 2,397,545 | 4/1946 | Hardinge | 606/65 |
| 3,779,239 | 12/1973 | Fischer et al. | 606/62 |
| 4,846,162 | 7/1989 | Moehring | 606/67 |
| 4,858,602 | 8/1989 | Seidel et al. | 606/60 |
| 4,978,349 | 12/1990 | Frigg | 606/67 |
| 5,035,697 | 7/1991 | Frigg . | |
| 5,112,333 | 5/1992 | Fixel | 606/62 |
| 5,154,719 | 10/1992 | Cotrel | 606/72 |
| 5,176,680 | 1/1993 | Vignaud et al. | 606/60 |
| 5,263,955 | 11/1993 | Baumgart | 606/62 |

FOREIGN PATENT DOCUMENTS

| | | |
|---|---|---|
| 0023228 | 2/1981 | European Pat. Off. . |
| 2701279 | 7/1977 | Germany . |
| 8533134 U | 5/1986 | Germany . |
| 8811634 U | 2/1990 | Germany . |
| 9101035 U | 5/1991 | Germany . |
| 9100065 | 1/1991 | WIPO . |

*Primary Examiner*—Stephen O. Pellegrino
*Assistant Examiner*—Jeffrey A. Schmidt
*Attorney, Agent, or Firm*—Peter C. Richardson; Lawrence C. Akers; Elizabeth O. Slade

[57] ABSTRACT

A bone nail for the medical care of spoke bone (i.e., radius) fractures comprises a hollow shaft (10) curved in a plane, which shaft is to be distally and posteriorly inserted into a spoke bone medullary canal and which includes a proximal end portion which is slotted so as to be able to be spread apart by a spreading body. A straddling member (36) having an outer threaded portion (44) cooperates with an inner threaded portion (18) in the slotted portion (12) of the shaft (10) of the nail so as to radially expand the proximal nail end when the straddling body (36) is rotated. A cross bore (22) at the distal end of the shaft (10) receives a bone screw extending approximately vertical to the plane of the curvature.

12 Claims, 2 Drawing Sheets

BONE NAIL FOR SPOKE BONE FRACTURES

The present invention refers to a bone nail for the medical care of spoke bone fractures.

A variety of nails to be anchored in the medullary cavity is known in the medical care of hollow bone fractures. Particularly useful are so-called locking nails to statically fix fractional fragments by means of cross bolts. Locking nails of this type are primarily used for the femur and the tibia. German petty patent DE-GM 85 34 358 discloses a bone nail for upper arm fractures, which nail is slotted at its distal end to be expanded by a spreading body cooperating with an internal thread of the nail shaft. The known upper arm nail is thus proximally inserted and distally anchored by the spreading body. An anchoring of this type by forming one end of a bone nail as a spreading dowel is known from European patent EP 0 023 228.

A bone nail for the medical care of fractures of the human radius or spoke bone has not yet become known. An object of the invention is to provide an intra-medullary bone nail which is suited for the medical care of bone spoke fractures.

These and other objects are solved by the features of the bone nail of the invention.

According to the invention the bone nail comprises a hollow nail shaft curved in a plane which shaft is slotted at its proximal end to be spread apart by a spreading body. The bone nail is distally and posteriorly inserted and will be thus proximally locked like a straddling dowel. A further locking is provided by a bone screw which extends through a cross bore in the distal end of the shaft. The cross bore approximately extends normally to the curved plane of the nail. The curvature of the nail corresponds to the anatomic curvature of the spoke bone; however, the nail has to be inserted such that it is turned about 90° about its longitudinal axis while being driven in.

According to a further embodiment of the invention the cross bore is defined by an elongate opening. This makes possible a dynamic process, i.e. the bone fragments may drift relatively with respect to each other in a longitudinal direction, but are locked in the rotational direction. When the distal end of the nail shaft is provided with an internal thread receiving a screw bolt, a pressure may be exerted on the nail screw. Accordingly the nail of the present invention may be used as a compression device.

According to a still further embodiment of the invention the internal threaded portion of the proximal end preferably extends towards both sides of the end of the slotted portion.

According to a further feature of the invention the proximal end portion of the shaft is formed straight to suit anatomic conditions. In a further embodiment, the invention provides for at least a recess in the distal end of the shaft. The recess serves to apply a tool to perform the rotation above referred to in driving in the nail. To detect the cross bore after driving in the nail, a positioning unit is used which alike may cooperate with the distal end. The recess serves to fix the rotational position of the positioning device with respect to the nail shaft.

In a further embodiment of the invention, opposite flats in the distal end portion of the shaft are provided which flats are located approximately parallel to the plane of the curve. When the nail is in its end position, the flats lie approximately parallel to the back of the hand so that the distal end of the nail is as little bulky as possible.

Still further, the distal end portion of the shaft is slightly expanded like a trumpet, preferably extending from the cross bore up to the distal end. Due to anatomic conditions the nail shaft mast have a limited diameter. It is thus difficult to apply a suitable tool to the distal end. By flaring the distal end, the application of a driving and manipulating tool and of the positioning device is facilitated. The transfer of axial blows and torque to the nail is improved by flaring the nail.

According to a further feature of the invention, the length of the nail shaft is selected such that its proximal end portion is located in the area of the tuberositas radii. In this area, the spoke bone is relatively pressure stable and has an approximately oval cross section so that fracturing the bone by straddling the nail is minimized. Of course, a variety of nail lengths may be provided, preferably in steps of 10 mm, for example.

According to a further embodiment of the invention, the spreading body comprises a cap, preferably made of metal, which cap is rotatably but axially fixed on the straddling body formed as a screw bolt and comprising a conical straddling face. By this, a friction occurs between the straddling body and the nail shaft in axially shifting but not in rotating. This makes it possible to gently and effectively straddle the proximal nail end.

Figure 2:
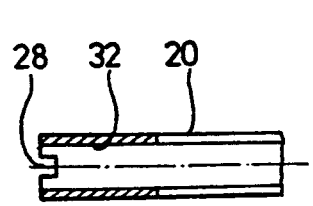
Figure 3:
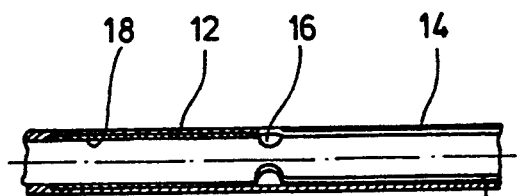
Figure 4:
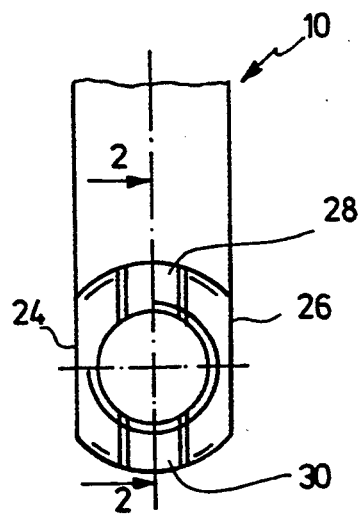
Figure 5:
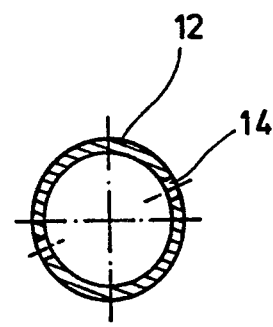
Figure 6:
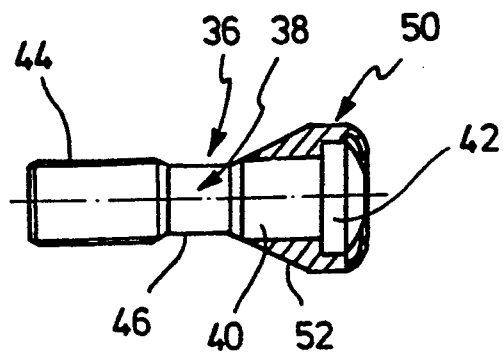
Figure 7:
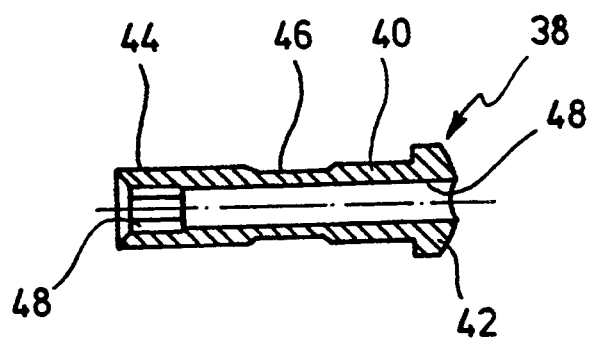
Figure 8:
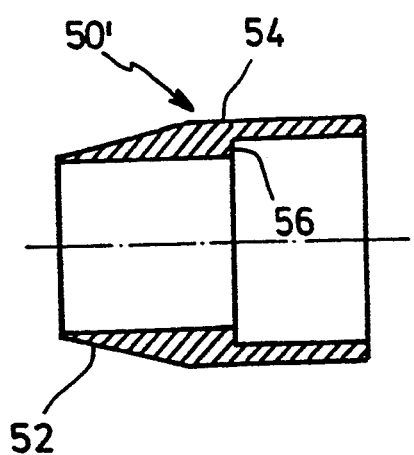

An embodiment of the invention is described in detail in referring to the drawings which show:

FIG. 1 a side view of a bone nail according to the invention,

FIG. 2 a section through the distal end of the bone nail of FIG. 1 along the line 2—2 in FIG. 4, FIG. 3 a section through the nail of FIG. 1 along the line 3—3, FIG. 4 an end view of the bone nail of FIG. 1 in the direction of arrow 4, FIG. 5 a section through a nail of FIG. 1 along the line 5—5, FIG. 6 a view of a straddling body for the nail of FIG. 1, FIG. 7 a section through the screw bolt of the straddling body of FIG. 6 and FIG. 8 a section in an enlarged scale of a blank forming a cap for the straddling body of FIG. 6.

A hollow nail shaft 10 made of a body-compatible material of suitable strength is curved in a plane, wherein the proximal end portion 12 is formed straight. The proximal end portion 12 further includes a pair of diametral slots 14 separating the proximal end portion in a pair of straddling tongues. The slots distally end in circular enlargements 16 to stress-relieve the material when being straddled. The proximal end portion 12 is provided with an internal threaded portion 18 extending at both sides of the distal ends of the slots 14. In the distal end portion 20 the shaft 10 includes a cross bore 22 which is formed as an elongated opening extending approximately perpendicular to the curvature plane of the shaft 10. Distal with respect to the bore 22, the end portion 20 is trumpet-like enlarged, but only in the curvature plane as is clearly seen from FIGS. 2 and 4. The distal end portion of the nail is oval, and a pair of opposite flats 24 and 26 is provided at a distance apart which approximately corresponds to the diameter of the nail shaft 20 in the remaining portion, while the remaining portion of the nail is circular. A pair of diametral recesses 28, 30 is provided at the end. The distal end portion further includes an internal thread 32.

The nail shaft 10 is posteriorly inserted in the area of the back of the hand, wherein a spreading body 36 is received in the proximal end 12. The spreading member is described in referring to FIGS. 6 to 8.

A bolt 38 has a shaft 40 including a head 42 and a threaded portion 44 at the opposite end. In the central portion the shaft 40 is grooved at 46. As seen from FIG. 7, the shaft 40 is provided with a through bore 48. At its distal end the shaft 40 is provided with an internal hexagon 48 or something similar for applying a tool. A straddling cap 50 sits over the shaft 40 and the head 42, which blank 50' is shown in FIG. 8. The blank is made of metal and its end includes a conical straddling face 52 Joining a cylindrical face 54. The hollow blank 50' further includes an internal shoulder 56. The blank 50' is pushed over the bolt 38 from the threaded portion 44 until the shoulder 56 contacts the underside of the head 42. Subsequently, the remaining portion of the blank is shaped partly around the head so that the cap 50 may not fall off the bolt 38.

Inserting the nail shaft 10 is performed when the straddling member 36 is mounted, wherein the threaded portion 44 is received by the internal thread 18 of the proximal end portion 12 and the cap 50 is partly located outside of the nail 10. Driving in the nail by a driving unit which cooperates with the distal nail end 20 and which engages the recesses 28, 30, is initially started in a position in which the plane of the curvature of the nail shaft is offset approximately 90° with respect to the natural curvature of the spoke bone. During the driving process, the nail shaft is rotated about approximately 90° by means of the driving device. Subsequently, the nail reaches a position in which the flats 24, 26 extend approximately parallel to the back of the hand. Driving in may be performed by a lance which has been driven before into the spoke bone. For this the screw bolt 38 has a through-bore 48. After the nail shaft 10 has been driven in and properly positioned, the screw bolt 38 is rotated by inserting a tool through the hollow nail shaft 10. The tool cooperates with the hexagon 48. In axially displacing the bolt, the conical face 52 expands the end portion 12 to proximal anchor the nail 10. Then the position of the cross bore 20 is determined by a positioning unit to provide a bore in the bone to fix a bone screw which is preferably inserted close to the distal end of the cross bore 22. By turning a screw (not shown) in the internal thread 32, the screw presses against the bone screw in the cross bore 22 to compress the bone fragments.

The positioning device may cooperate with the axial recesses 28, 30 to obtain a proper rotational position with respect to the nail shaft 10.

The outer diameter of the nail shaft 10 is preferably 5 or 6 mm and the inner diameter about 2.5 to 4 min. The length may be 170 to 250 mm in steps of 10 mm, for example. The length is preferably selected such that straddling is performed in the area of the tuberositas radii which is a relatively strong section of the spoke bone. Further, the nail cross-section is approximately oval to facilitate the deformation of the proximal nail end.

We claim:

1. A bone nail for the medical care of spoke bone fractures comprising a hollow shaft (10) curved in a plane with a curvature which corresponds substantially to the anatomic curvature of a spoke bone, which shaft is to be distally inserted in the medullary cavity and which includes a proximal end which is slotted by at least one slot 14, a straddling member (36) having an outer threaded portion (44) cooperating with an inner threaded portion (18) in the slotted portion (12) of said nail shaft so as to radially expand the proximal nail end by rotating the straddling body (36), and a cross bore (22) at the distal end of the shaft (10) to receive a bone screw extending approximately vertical to the plane of the curvature, wherein said cross bore is formed by an elongated opening (22), wherein the inner threaded portion extends at both sides of the distal ends of a first slot and a second slot 14, wherein the proximal end portion (12) of the shaft (10) is formed straight, wherein an inner threaded portion (32) is formed in the distal end portion (20), wherein said distal end (20) of the shaft comprises at least a recess (28, 30), and wherein the distal end portion of the shaft (10) comprises opposite flats (24, 26) extending approximately parallel to the plane of the curvature.

2. The bone nail of claim 1, wherein the distal end portion of the shaft (10) tapers slightly trumpet-like from the cross bore (22) towards the distal end.

3. The bone nail of claim 2, wherein said shaft (10) has a length within the range from 170 to 250 mm and has a cross-section which is approximately oval.

4. The bone nail of claim 3, wherein the straddling body (36) has located therein an axial through bore (48).

5. The bone nail of claim 4, wherein the straddling body (36) further comprises a cap (50) preferably made of metal which is rotatably mounted but axially fixed on a screw bolt (38), and that the straddling body (36) includes a conical straddling face (52).

6. The bone nail of claim 5,
   wherein the proximal end portion (12) comprises a pair of diametral opposite slots (14).

7. A bone nail for repairing spoke bone (i.e., radial bone) fractures of the arm, said nail to be inserted distally into a spoke bone medullary canal, said nail comprising: (a) a hollow shaft having a proximal end portion, a distal end portion, and a central portion, wherein said shaft is curved in a plane P and curved with a curvature which corresponds substantially to the anatomic curvature of a spoke bone and wherein said proximal end portion has a first slot with a proximal slot end and a distal slot end and wherein said proximal end portion has a first inner threaded portion; (b) a straddling member adapted to be moved into said proximal end portion, said straddling member having an outer threaded portion which cooperates with said first inner threaded portion so as to radially expand said proximal end portion when said straddling body is rotated; and (c) a cross bore located near said distal end of said shaft for receiving a bone screw to be implanted into a spoke bone at an angle approximately perpendicular to said plane P, wherein said cross bore is formed by an elongated opening, wherein said proximal end portion is substantially straight, wherein said distal end portion has a second inner threaded portion, wherein said distal slot end has a first side and a second side, wherein said first inner threaded portion extends toward both said first side and said second side, wherein said distal end portion has located therein at least one recess, and wherein said distal end portion comprises opposite flat parallel surfaces extending approximately parallel to said plane P.

8. A bone nail according to claim 7, wherein said distal end portion tapers slightly in a trumpet-like manner from said cross bore towards the end of said distal end portion.

9. A bone nail according to claim 8, wherein said shaft has a length within the range from 170 to 250 mm and has a cross-section which is approximately oval.

10. A bone nail according to claim 9, wherein said straddling body has located therein an axial throughbore.

11. A bone nail according to claim 10, wherein said straddling body further comprises a cap which is rotatably mounted but axially fixed on a screw bolt and wherein said straddling body comprises a conical straddling face.

12. A bone nail according to claim 11, wherein said proximal end portion further includes a second slot positioned diametrically opposite to said first slot.

* * * * *